United States Patent
Prohaska et al.

(10) Patent No.: US 7,013,707 B2
(45) Date of Patent: Mar. 21, 2006

(54) METHOD AND APPARATUS FOR ENHANCED DETECTION OF A SPECIE USING A GAS CHROMATOGRAPH

(75) Inventors: Otto J. Prohaska, Seymour, CT (US); Avinash Dalmia, Hamden, CT (US); Andrew Tipler, Trumbull, CT (US)

(73) Assignee: PerkinElmer LAS, Inc, Boston, MA (US)

( * ) Notice: Subject to any disclaimer, the term of this patent is extended or adjusted under 35 U.S.C. 154(b) by 69 days.

(21) Appl. No.: 10/345,608

(22) Filed: Jan. 16, 2003

(65) Prior Publication Data

US 2003/0164312 A1 Sep. 4, 2003

Related U.S. Application Data

(63) Continuation-in-part of application No. 09/443,875, filed on Nov. 19, 1999, now Pat. No. 6,682,638.

(51) Int. Cl.
*G01N 27/26* (2006.01)
*G01N 27/407* (2006.01)
*G01N 30/62* (2006.01)

(52) U.S. Cl. .................. 73/23.4; 73/23.35; 204/421; 204/424; 204/426; 204/431; 205/783.5; 422/89; 436/161

(58) Field of Classification Search .............. 73/23.35, 73/23.4, 23.41; 204/421, 424, 426, 431; 422/83, 89, 98, 99; 436/161; 205/783.5
See application file for complete search history.

(56) References Cited

U.S. PATENT DOCUMENTS

| | | |
|---|---|---|
| 3,934,193 A | 1/1976 | Hall |
| 3,972,682 A | 8/1976 | Stephens et al. |
| 4,032,296 A | 6/1977 | Hall |
| 4,038,053 A | 7/1977 | Golay |
| 4,172,770 A | 10/1979 | Semersky et al. |
| 4,440,726 A | 4/1984 | Coulson |
| 4,555,383 A | 11/1985 | Hall |
| 4,032,296 A | 1/1987 | Hall |
| 4,649,124 A | 3/1987 | Hall |
| 4,812,221 A | 3/1989 | Madou et al. |
| 4,820,386 A | 4/1989 | LaConti et al. |
| 4,851,104 A | 7/1989 | Connery et al. |

(Continued)

FOREIGN PATENT DOCUMENTS

DE 199 40 095 A1 1/2001

(Continued)

OTHER PUBLICATIONS (Polyaniline thin-films for gas sensing), N.E. Agbor et al., 1995 Elsevier Science S.A. pp. 173-179.

(Continued)

*Primary Examiner*—Daniel S. Larkin
(74) *Attorney, Agent, or Firm*—St.Onge Steward Johnston & Reens

(57) ABSTRACT

The invention includes a method and apparatus for a chromatography system having a chromatographic column for separating gases in a mixture from one another and an electrochemical gas sensor coupled to the chromatographic column for detecting a gas being emitted from the column. The electrochemical gas sensor further includes a substrate having a surface for depositing electrodes thereon, an ionomer membrane in contact with the surface, an electrode in contact with the surface, and an opening in the ionomer membrane in a location proximate to the electrode for permitting a gas to diffuse through the opening to simultaneously contact the electrode and the ionomer membrane within the opening.

16 Claims, 6 Drawing Sheets

U.S. PATENT DOCUMENTS

| | | | |
|---|---|---|---|
| 4,888,295 A * | 12/1989 | Zaromb et al. | 436/161 |
| 4,900,405 A | 2/1990 | Otagawa et al. | 204/412 |
| 5,194,814 A | 3/1993 | D'Couto | |
| 5,302,274 A | 4/1994 | Tomantschger et al. | |
| 5,331,310 A | 7/1994 | Stetter et al. | |
| 5,525,197 A | 6/1996 | Coulson | |
| 5,527,446 A | 6/1996 | Kosek et al. | |
| 5,545,252 A | 8/1996 | Hinshaw et al. | |
| 5,573,648 A | 11/1996 | Shen et al. | |
| 5,650,054 A | 7/1997 | Shen et al. | |
| 5,711,786 A | 1/1998 | Hinshaw | |
| 5,830,337 A | 11/1998 | Xu | |
| 5,889,197 A | 3/1999 | Van der Maas et al. | |
| 5,985,673 A | 11/1999 | Bao et al. | |
| 6,080,294 A | 6/2000 | Shen et al. | |
| 6,165,251 A | 12/2000 | Lemieux et al. | |
| 6,200,443 B1 | 3/2001 | Shen et al. | |
| 6,205,841 B1 | 3/2001 | Shibamoto | |
| 6,245,298 B1 | 6/2001 | Bremer et al. | |
| 6,287,643 B1 | 9/2001 | Powell et al. | |
| 6,306,489 B1 | 10/2001 | Hellman et al. | |
| 6,309,612 B1 | 10/2001 | Balachandran et al. | |
| 6,338,823 B1 | 1/2002 | Furakawa | |
| 6,355,150 B1 | 3/2002 | Savin-Poncet et al. | |

FOREIGN PATENT DOCUMENTS

| | | |
|---|---|---|
| DE | 199 44 650 A1 | 12/2001 |
| EP | 0 157160 A1 | 9/1985 |
| GB | 1382640 | 6/1972 |
| GB | 1382649 | 8/1972 |

OTHER PUBLICATIONS (The Development of a Thick-Film Electrochemical Sensor and Instrumentation for In-Situ Determination of Carbon Dioxide Partial Pressure ($pCO_2$) In The Marine Environment), M.R. Creasey et al., University of Southampton, U.K., Electronic Engineering in Oceanography, Jul. 19-21, 1994, Conference Publication No. 394 IEE 1994.
(Sixth International Conference on Electronic Engineering in Oceanography) Electron theory of thin-film gas sensors, Helmut Geistlinger, 1993 Elsevier Sequoia, pp 47-60.
(A Practical Reference Electrode) J. Giner, Pratt & Whitney Aircraft, Division of United Aircraft Corporation, East Hartford, CT.
(Design and application of thick-film multisensors) N. Hampp et al., 1992 Elsevier Sequoia pp. 144-148.
(Thin Film Porous Membranes for Catalytic Sensors) R.C. Hughes, et al., 1997 International Conference on Solid-State Sensors and Actuators Chicago, Jun. 16-19, 1997.
(Amperometric Gas Sensor of Thin Gold Film Electrode Ion-Plated on Gas Permeable Membrane for Detection of Arsine and Silane) Toru Ishiji et al., pp. 1019-1020.
(A solid-state pH sensor based on a Nafion-coated iridium oxide indicator electrode and a polymer-based silver chloride reference electrode) Patrick J. Kinlen et al., 1994 Elsevier Science pp 13-25.
(Multifunctional Sensors Based on Ceramic Electrolytes) Meilin Liu et al., Georgia Institute of Technology, Atlanta, Georgia pp 421-427.
(The thick-film route to selective gas sensors) F. Menil et al., 1995 Elsevier Science S.A. pp 415-420.
(Properties of vanadium oxide thin films for ethanol sensor) G. Micocci et al., J. Vac. Sci. Technol. A 15(1), Jan./Feb. 1997 American Vacuum Society.
(An Integrated Multi-Element Ultra-Thin-Film Gas Analyzer) N. Najuh et al., Solid-State Sensor and Actuator Workshop Proc. 5.
(Preparation of thin gold-film electrode for an electrochemical gas sensor for phosphine and arsine) Nobuo Nakano, et al., 1994 Elsevier Science S.A. pp 51-55.
(A Study of the Surface Sensitivity of Tin Oxide Sensors To Carbon Monoxide and Dioxide) Dario Narducci et al., Dept. of Physical Chemistry & Electrochemistry v. C. Golgi, 19 I-20133 Milano (Italy).
(UV-Polymerizable Screen-Printed Enzyme Pastes) Ingrid Rohm, et al., 1995 American Chemical Society Analytical Chemistry, vol. 67, No. 13, Jul. 1, 1995, Anal. Chem. 1995, 67,2304-3207.
(CO-Sensor for domestic use based on high temperature stable $Ga_2O_3$ thin films), T. Schwebel, et al., 1997 International Conference on Solid-State Sensors and Actuators Chicago, Jun. 16-19, 1997.
(A Low-Power CMOS Compatible Integrated Gas Sensor Using Maskless Tin Oxide Sputtering) Lie-yi Sheng, et al., 1997 International Conference on Solid-State Sensors and Actuators Chicago, Jun. 16-19, 1997 pp 939-942.
(Platinum Thin Films and Next-Generation Micromachined Sensors) John Staley, et al., Sensors Apr. 1996.
(An amperometric carbon monoxide sensor based on the steady-state difference response technique) Y. Tan et al., 1995 Elsevier Science S.A. pp 113-121.
(A Novel Semiconductor No Gas Sensor Operating At Room Temperature) Zhang Wenyi et al., 1997 International Conference on Solid-State Sensors and Actuators, Chicago, Jun. 16-19, 1997.
(Environmental gas sensing) Noboru Yamazoe et al., 1994 Elsevier Science S.A. pp 95-102.
(Life-elongation mechanism of the polymer-electrolyte lamination on a CO sensor) Ayumu Yasuda, et al., 1994 Elsevier Science S.A. pp 229-236.
Analytik Jena AG acquires 100% of APS Technologies, Inc./USA Jena/Houston, Sep. 24, 2001, 2 pgs.
Total Sulfur Analyzer—Combustion / Electrochemical Detection*; APS Technologies, Inc.; ASTM D6428-99; 40 CFR 80.580; 2 pgs.
Versatile Electrolytic Conductivity Detector For Gas Chromatography, P. Jones and G. Nickless, J. Chromatogr., 73 (1972), 19-28.
Electrolytic Conductivity Detector for Gas Chromatography, Dale M. Coulson, Coulson Instruments Co., J. Gas Chromatography, Apr. 1965.
Carbon Monoxide Sensors, Beech et al., Electrochemistry at Loughborough, 1999.

* cited by examiner

METHOD AND APPARATUS FOR ENHANCED DETECTION OF A SPECIE USING A GAS CHROMATOGRAPH

PRIORITY APPLICATION

This application is a continuation in part of U.S. patent application Ser. No. 09/443,875 for "Film Type Solid Polymer Ionomer Sensor and Sensor Cell" filed Nov. 19, 1999, now U.S. Pat. No. 6,682,638.

FIELD OF THE INVENTION

The invention relates to a gas chromatograph and detection unit for tecting minute quantities of a gas specie.

BACKGROUND OF THE INVENTION

Gas chromatography is essentially a method of separation of mixtures of substances into their individual components. In a typical analysis of a sample by a gas chromatograph, the sample is introduced into a chromatographic column together with a carrier gas. At the end of the column the individual components are more or less separated in time. Generally, detection of the gas provides a time-scaled pattern which, by calibration or comparison with known samples, indicates the constituents of the test sample.

Separation of the sample usually occurs within the column upon interaction with the stationary phase, whereby the distribution coefficients of the elements may cause the separation. Typically, the constituents of a test sample in a carrier gas are adsorbed and desorbed by a stationary phase material in a column. Polarity may also play a role in separating the components from one another over time. Differences in polarites may cause the components to attach to the stationary phase at different intervals. Elements exiting the column are typically detected by a detector and the results are usually charted, often resulting in a chromatogram.

For gases that may have difficulty being detected by the detector, the system for the gas chromatography may optionally include a reactor, which generally heats the desired gas with a reactant to form a detectable compound. The reactant may be a gas, liquid, or solid and varies according to the desired gas to be detected. Typical reactants include air, hydrogen, and oxygen. A detectable compound is one that generally provides an electrical signal detectable by the detector.

Typical detectors for measuring the gases exiting the column include mass spectrometers and electrolytic conductivity detectors. Other detection systems include thermal conductivity, flame ionization and argon detectors. Electrolytic conductivity detectors usually provide an electrical signal that is functionally related to the presence of a selected element.

Electrolytic conductivity detectors are known for investigating the properties of electrolytes in solutions. Such devices typically include electrode surfaces with a continuous phase liquid electrolyte therebetween. These detectors may entail measuring a difference in resistance in the electrolytic material before and after the gas exiting the column enters the detector and is absorbed by the electrolytic material. If the gas was mixed with a reactant in the reactor, the reactant may also be absorbed in the electrolytic material before providing a detectable electrical signal. A possible disadvantage of the conductivity detector is that absorption by the electrolytic material takes time, which lengthens the detector's response time. The disadvantage may be exacerbated if both the gas and reactant need to be absorbed. Another possible disadvantage is the limited accuracy of the detector. Because the gas is detected indirectly, where the difference in resistance of the electrolytic material may indicate the type and/or concentration of the gas, a standard of deviation in the measurement error between the electrolytic material measurement and correlation from this measurement to the gas may negatively affect accuracy.

A typical conductivity detector is described in U.S. Pat. No. 4,440,726 to Coulson and shown in FIG. 1. As shown, an electrolyte, reactant gas, and gas exiting from the column enter the capillary. Electrodes 24 and 28 are placed in the electrolyte solution which may measure the difference in resistance.

Similar to the conductivity detector, the mass spectrometer and other detection systems of gas chromatography have potentially limiting abilities to detect gas with a high degree of sensitivity. As mentioned in U.S. Pat. No. 6,165,251 to Lemieux et al., gas chromatography systems in general have insufficient sensitivity to measure amounts of volatiles in the parts per billion concentration range.

What is desired, therefore, is a gas chromatography system having a detector with improved sensitivity. Another desire is provide a gas chromatography system that detects gas in the parts per billion concentration range. What is also desired is a gas chromatography system having an improved response time.

SUMMARY OF THE INVENTION

Accordingly, it is an object of the invention to provide a gas chromatography system having improved detection capabiltities.

It is another object of the invention to a gas chromatography system having a sensitivity in the parts per billion range.

It is a further object of the invention to provide a gas chromatography system having an improved response time.

These and other objects of the invention are achieved by provision of a chromatography system having a chromatographic column for separating gases in a mixture from one another and an electrochemical gas sensor coupled to the chromatographic column for detecting a gas emitted from the column. The electrochemical gas sensor further includes a substrate having a surface for depositing electrodes thereon, an ionomer membrane in contact with the surface, an electrode in contact with the surface, and an opening in the ionomer membrane in a location proximate to the electrode for permitting a gas to diffuse through the opening to simultaneously contact the electrode and the ionomer membrane within the opening.

For instances where a gas emitting from the column is difficult to detect, such as a gas that is not electrochemically active, the gas may be oxidized and/or reduced by a reactor prior to entering and being detected by the electrochemical gas sensor. Hence, a reactor may optionally be placed between and coupled to both the chromatographic column and the electrochemical gas sensor for facilitating oxidation and/or reduction.

The opening in the ionomer membrane may further extend from a first surface to a second surface of the ionomer membrane for defining walls to facilitate guiding the gas to the electrode. Additionally, the electrochemical gas sensor may include a housing for containing the substrate, the ionomer membrane, and the electrode. The housing may include a gas diffusion passage in a location proximate to the electrode and having fluid connection with the opening. In some embodiments, the gas diffusion passage is angled or misaligned with in relation to the opening.

In some embodiments, the substrate may include at least one hole extending from a first surface to a second surface of the substrate for permitting moisture to diffuse through the at least one hole to contact the ionomer membrane.

To enhance sensitivity, the ionomer membrane may be wetted with a solution or moisture. Hence, the sensor may include a reservoir containing the moisture or solution. In some embodiments, the reservoir is located adjacent to the substrate and on a side of the substrate opposite the ionomer membrane. In these embodiments, moisture from the reservoir diffuses through the at least one hole in the substrate to wet the ionomer membrane.

To facilitate diffusion of the moisture from the reservoir through the at least one hole, the sensor may have a wicking material in contact with the second surface of the substrate for drawing moisture from the reservoir toward said substrate. In addition to, or instead of placing the wicking material in this position, the wicking material may be located in the at least one hole of the substrate.

To reduce diffusion time for the moisture from the reservoir, the substrate's thickness may be reduced, wherein said substrate is a foil.

In another aspect of the invention, a method for detecting a gas in a gas chromatography system is provided. The method includes the steps of eluting a gas from a chromatographic column, coupling an electrochemical gas sensor to the chromatographic column, and detecting gas in an approximately parts per billion range.

In situations where the gas emitted from the chromatographic column is difficult to detect, the method may further include the step of oxidizing and/or reducing the gas. To carry this step out, the method may add a reactant to the emitted gas and provide a reactor to heat both the gas and the reactant during oxidation/reduction.

In another aspect of the invention, a method for detecting a gas in a gas chromatography system is provided, including the steps of eluting a gas from a chromatographic column, providing a substrate having a surface, depositing an electrode on the surface, contacting the electrode with an ionomer membrane, providing an opening in the ionomer membrane in an approximate area of the electrode, introducing the gas into the opening toward the electrode, and simultaneously contacting the gas with both the electrode and ionomer membrane.

The method may further include the step of providing a housing and a gas diffusion passage in the housing in the approximate area of the electrode. Both the opening in the ionomer membrane and the passage in the housing guide gas toward the electrode as it is introduced into the sensor. The opening and passage, by varying their length and/or girth, may control the gas as it passes through the opening and gas diffusion passage toward the electrode.

Similarly, the method may also provide at least one hole in the substrate for diffusing moisture from a reservoir through the at least one hole to the ionomer membrane and control the amount of moisture passing through the at least one hole by varying its size.

The invention and its particular features and advantages will become more apparent from the following detailed description considered with reference to the accompanying drawings.

DETAILED DESCRIPTION OF THE DRAWINGS

Figure 1:
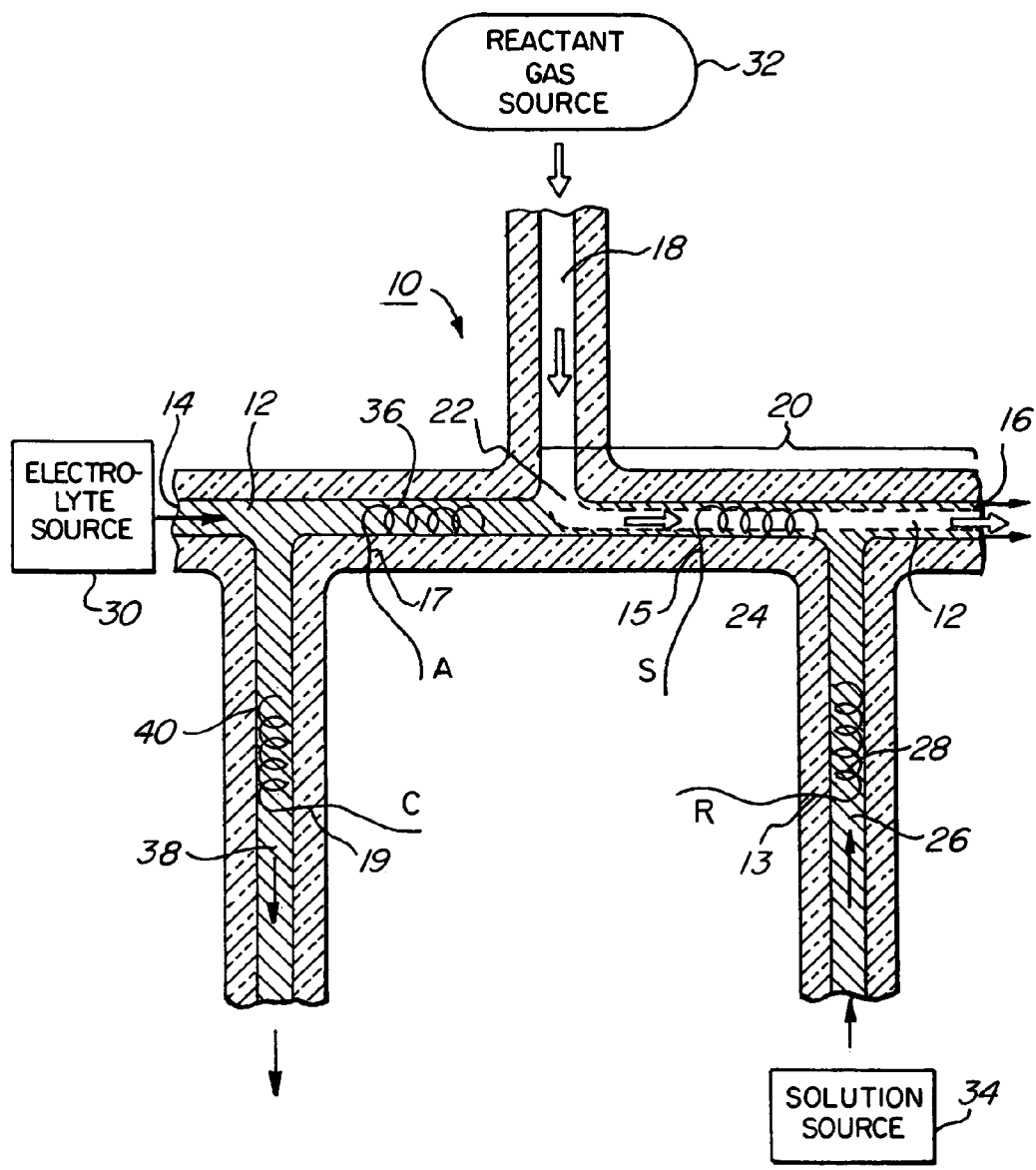
FIG. 1 depicts a conventional detector cell for electrochemical detection in accordance with the prior art.

FIG. 1 depicts a conventional detector cell for electrochemical detection. Cell 10 is typically placed at the exit of a gas chromatographic column and is usually formed from glass or other similar dielectric material. A first capillary extends horizontally from left to right across the cell 10. The first capillary 12 has an entrance 14 for an electrolyte solution and an exit 16 for the solution. A second capillary 18 intersects the first capillary 12, approximately midway between the entrance 14 and the exit 16 at right angles, to define a reaction zone 20 between the intersection 22 and the exit 16 from the first capillary 12. Coiled electrode 24 is positioned longitudinally in the reaction zone 20, along with the first capillary 12 at right angles, between the first electrode 24 and the exit 16 from the first capillary 12. A third capillary 26 intersects the first capillary 12 at right angles, between the first electrode 24 and the exit 16 from the first capillary 12. A second coiled electrode 28 is positioned longitudinally in the third capillary 26.

In use of the cell 10 for making potentiometric measurements, the entrance of the first capillary 12 is connected to an electrolyte source 30. The second capillary 18 is connected to a reactant gas source 32. The third capillary 26 is connected to a solution source 34, in order to establish a solution bridge between the first and second electrodes 24 and 28. In practice, the reactant gas source 32 may be a reactor tube, such as a pyrolysis tube for preconditioning the reactant in a reducing atmosphere, such as hydrogen gas, which may also contain a catalyst, such as nickel; a pyrolysis tube for preconditioning of the reactant in an oxidizing atmosphere, such as oxygen or air, which may also contain a catalyst, such as platinum; a photoionization tube in which chemical compounds are photochemically decomposed, a gas chromatographic column through any of the above reactor tubes; a pyrolysis tube furnace into which discrete samples are introduced; or the like.

With the elements of the detector cell 10 described so far, it is possible to carry out potentiometric measurements, utilizing the electrodes 24 and 28 to determine a resistance through the electrolyte solution supplied at entrance 14 and the reactant gas supplied through capillary 18, when they react in the reaction zone 20.

Because a measurement is made of the electrolyte solution across electrodes 24 and 28, the response time of cell 10 is limited to the time it takes for the specie to be absorbed and dispersed throughout the electrolyte solution so that the measurement is accurate. Measuring the solution before the specie has been absorbed and dispersed may result in a lower concentration of the specie in the solution than is actually present. This passage of time for proper absorption and dispersion increases cell response time and reduces sensitivity.

Further, cell 10 provides a limited capability for detecting minute quantities of a specie in the sample. This limited resolution, or detection capability, may be due to the absorption and/or dispersion technique or inherent in conventional detector cells 10.

Figure 2:
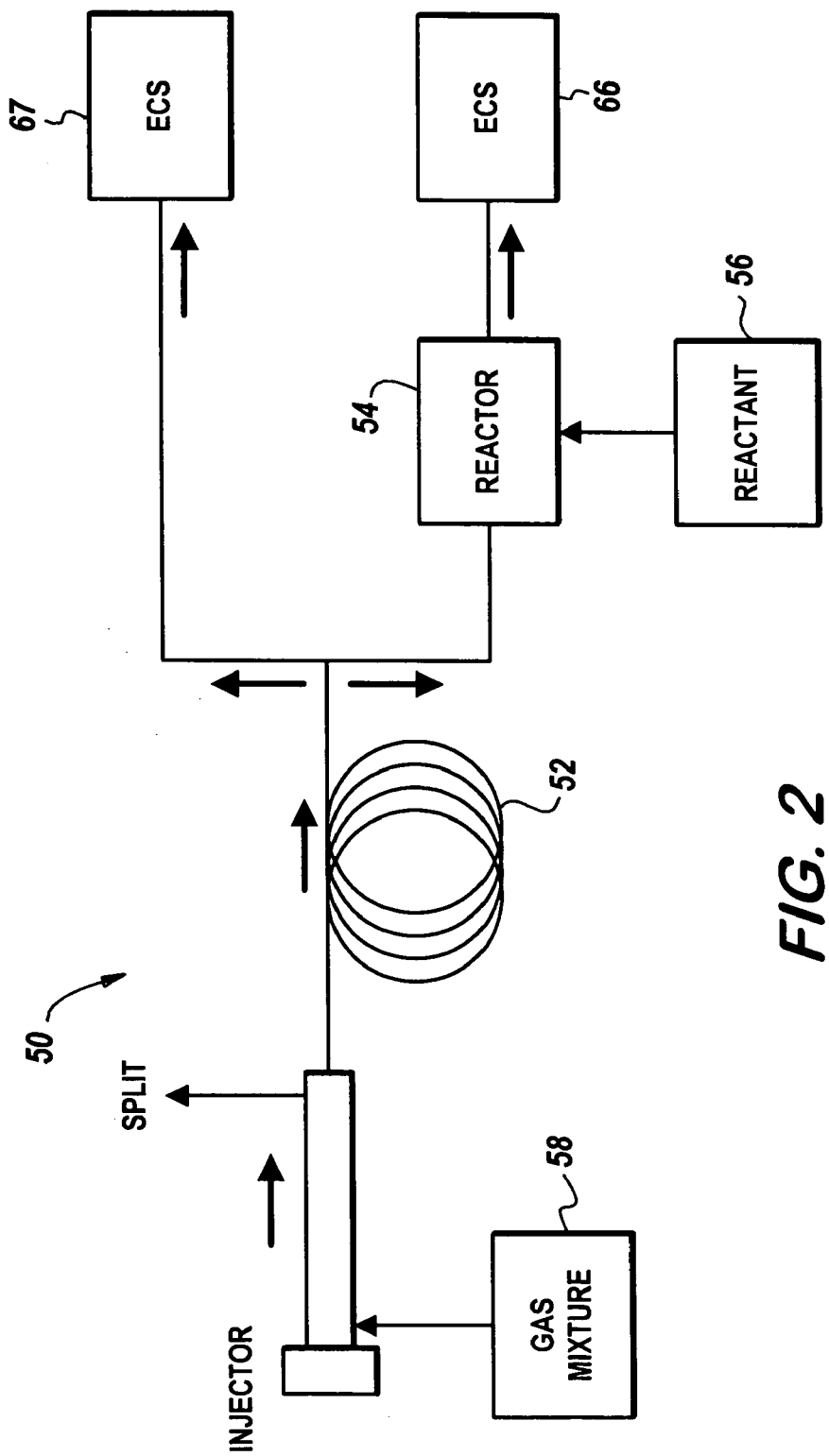
FIG. 2 depicts a chromatography system in accordance with the invention.

FIG. 2 depicts the system 50 for enhanced detection of a specie using a gas chromatograph in accordance with the invention. Similar to conventional systems for detecting a specie, a chromatographic column 52 is used to separate a sample of gas 58 into its respective components. The chromatographic column ("GC") 52 is not germane to the invention.

Upon exiting GC 52, each specie is detected by an electrochemical gas sensor 66, which is coupled to an end of GC 52 where the components, or species, are exiting GC 52. The combination of sensor 66 being coupled to GC 52 provides a system 50 for detecting a specie having enhanced sensitivity and response time because sensor 66 provides numerous advantages over conventional detector cells 10, as shown and described under FIG. 1.

Sensor 66 reduces the need for a specie of the sample to be absorbed and dispersed in an electrolyte solution in order for an electrical measurement to be taken across electrodes in contact with the solution. Sensor 66 detects gas as the gas comes in contact with an electrode, thereby reducing response time and increasing sensitivity. Moreover, the resolution, or detection capability, of sensor 66 is typically in the range of parts per billion, which is generally more sensitive than conventional detector cell 10 shown in FIG. 1. Sensor 66 is more particularly described under FIGS. 4 and 5.

System 50 further includes reactor 54, which is placed between sensor 66 and GC 52, for oxidizing and/or reducing a specie exiting GC 52 so that the specie may be detected by sensor 66. Typically, a specie desired to be detected by sensor 66, but which is not easily detectable, would be oxidized/reduced by reactor 54. As shown in FIG. 2, reactor 54 oxidizes/reduces a desirable specie of gas by heating the specie together with a reactant gas 56 at a specified temperature. Reactor 54 is not used to oxidize/reduce all species exiting GC 52 but is merely used to oxidize/reduce the particular specie(s) desired to be detected.

Species that are detectable by sensor 66 upon exiting GC 52 do not need to be oxidized/reduced. Hence, sensor 67 is coupled directly to GC 52. Sensor 66 and sensor 67 have all of the same limitations and advantages but are merely positioned in varying locations, whereby sensor 66 is downstream of reactor 54 and sensor 67 is directly downstream of GC 52. For the sake of simplicity, sensor 66 will be described hereinafter. Reactor 54 is not germane to the invention.

Figure 3:
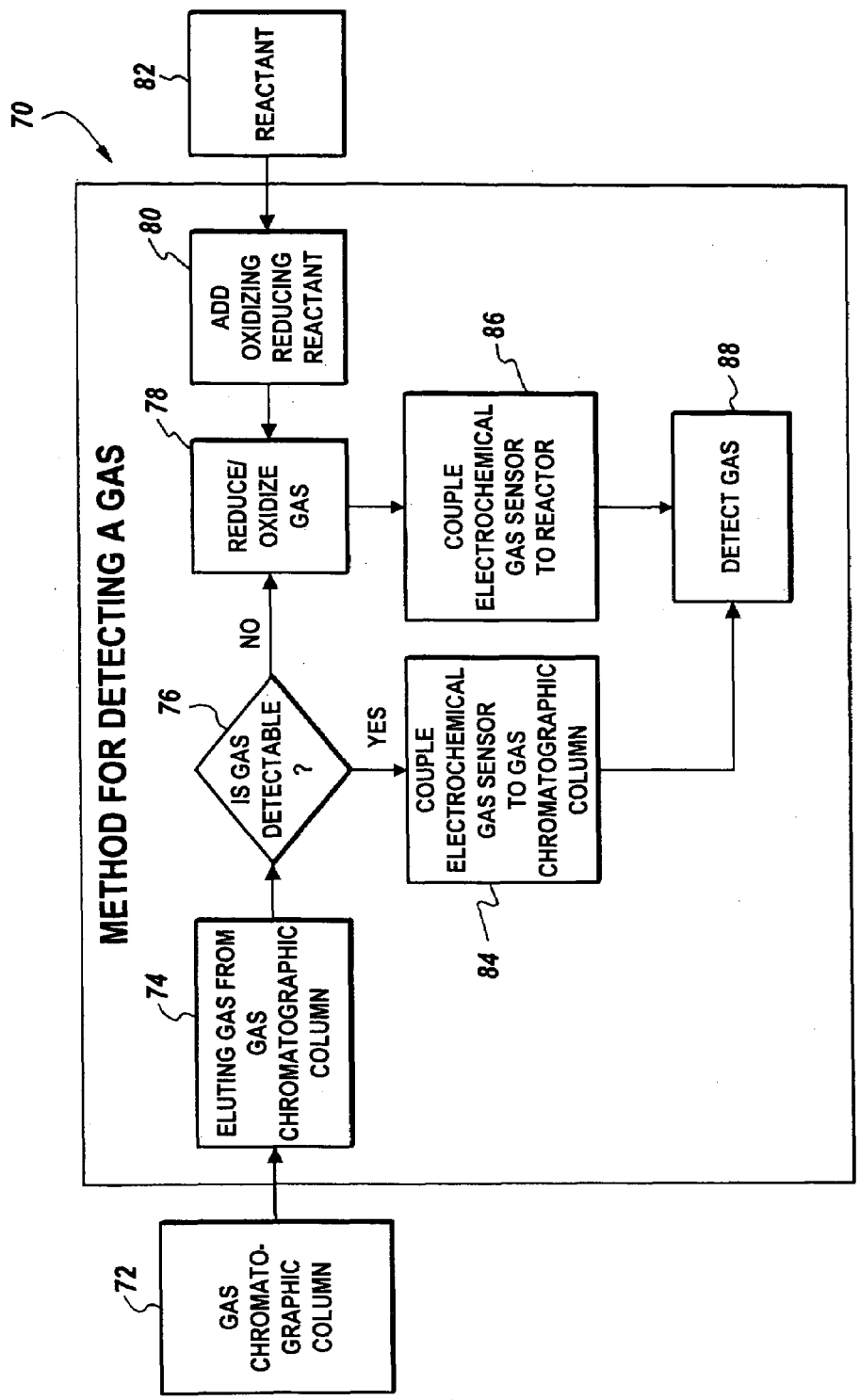
FIG. 3 depicts a method for providing the chromatography system of FIG. 2.

FIG. 3 depicts a method 70 for detecting a specie of gas using a gas chromatograph system. Method 70 includes the step of eluting 74 a gas component from a gas chromatographic column 72 and determining 76 whether or not the eluted gas component is detectable. The gas component is usually at least one specie of the gas entering column 72. Also, a user, operator, or computer system, such as a programmable logic controller or microprocessor, may make the determination as to the component's detectability.

If the eluted component is determined to be difficult to be detected by an electrochemical gas sensor, the component is then oxidized or reduced 78 by heating the component in a reactor to facilitate converting the component into an electrochemically active specie. During oxidation and/or reduction, method 70 adds a reducing or oxidizing agent 80, or reactant 82, such as oxygen or hydrogen. Upon being reduced and/or oxidized in the reactor, the gas component enters an electrochemical gas sensor for detection, the sensor being coupled 86 to the reactor. The gas component is then detected 88 by the sensor. The types of sensors that may be used in method 70 are more particularly described under FIGS. 4 and 5.

An example of reductive pyrolysis in a reactor is as follows:

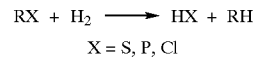
$$RX + H_2 \longrightarrow HX + RH$$
$$X = S, P, Cl$$

An example of oxidative pyrolysis in a reactor is as follows:

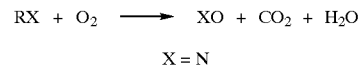
$$RX + O_2 \longrightarrow XO + CO_2 + H_2O$$
$$X = N$$

The corresponding reaction at the sensing (SE) and counter electrodes (CE) during oxidation and/or reduction is as follows:

Sensing Principle at Sensor

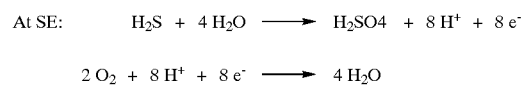
$$\text{At SE:} \quad H_2S + 4H_2O \longrightarrow H_2SO_4 + 8H^+ + 8e^-$$
$$2O_2 + 8H^+ + 8e^- \longrightarrow 4H_2O$$

If the eluted component is determined to be detectable without being oxidized/reduced, the gas component enters the electrochemical gas sensor directly upon exiting column 72. Hence, the electrochemical gas sensor is coupled 84 to column 72 without a reactor between the sensor and column 72. The gas component is then detected 88 by the sensor. The types of sensors that may be used in method 70 are more particularly described under FIGS. 4 and 5.

Figure 4:
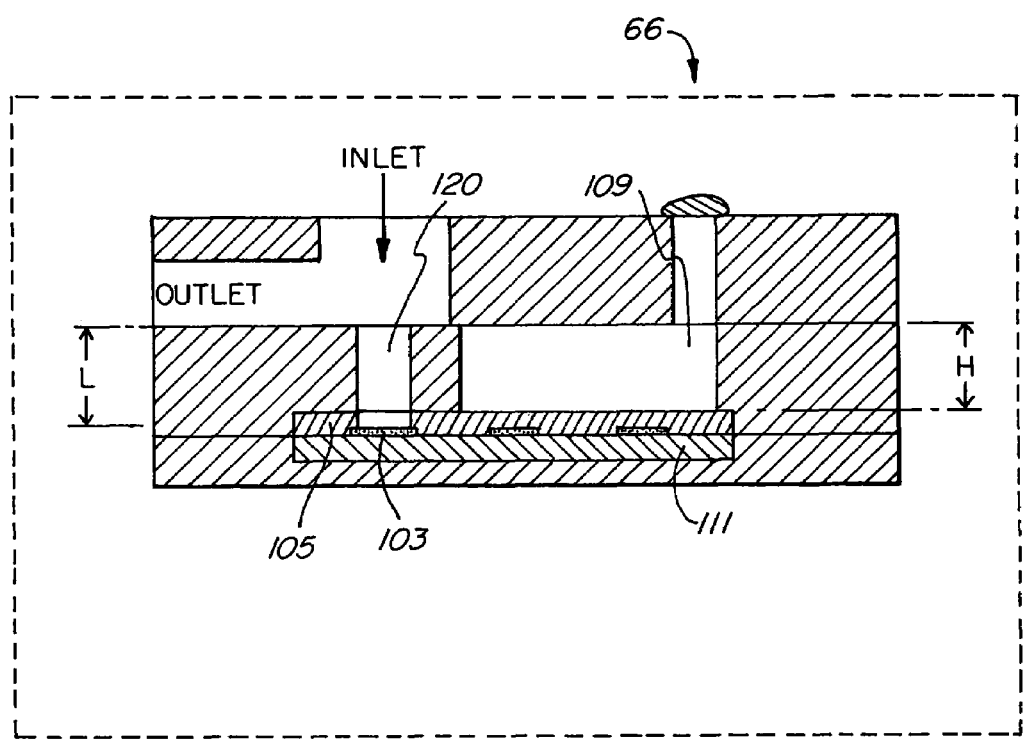
FIG. 4 depicts one embodiment of an electrochemical gas sensor used for the chromatography system of FIG. 2.

FIG. 4 shows an electrochemical gas sensor of copending U.S. patent application Ser. No. 09/443,875, now U.S. Pat. No. 6,682,638, which may be used as sensor 66. As shown, electrochemical gas sensor 66 includes substrate 111, electrode 103, and ionomer membrane 105. Gas enters and exits sensor 66 through the inlet and outlet as shown. A portion of the gas entering sensor 66 diffuses through diffusion hole 120 and contacts electrode 103, which detects the type of gas present in sensor 66. As stated above, for the purposes of simplicity, sensor 67 will not be described but is understood to include the limitations of sensor 66.

To enhance sensitivity to sensor 66, a reservoir 109 is provided containing electrolyte solution to wet ionomer membrane 105. As shown, reservoir 109 and, therefore, the electrolyte solution is in contact with ionomer membrane 105. Because reservoir 109 is located on a same side of ionomer membrane 105 as diffusion hole 120, a length of diffusion hole is typically at least as long as a height of reservoir 109.

Figure 5:
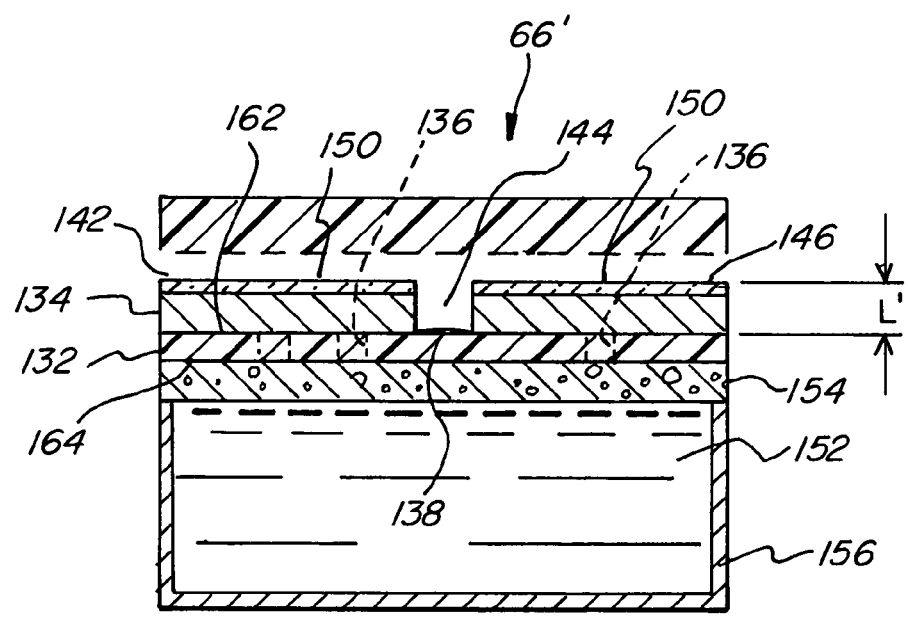
FIG. 5 depicts another embodiment of an electrochemical gas sensor used for the chromatography system of FIG. 2.

FIG. 5 depicts another embodiment of electrochemical gas sensor in accordance with the invention. Sensor 66' includes substrate 132, ionomer membrane 134, and electrode 138. Gas enters sensor 66' through inlet 142 and is detected after diffusing through diffusion hole 144 to contact electrode 138, which is in contact with ionomer membrane 134. Gas exits sensor 66' through outlet 146. It is understood that the gas may flow in a reversed direction where outlet 146 is the inlet and inlet 142 is the outlet.

To enhance the sensitivity of sensor 66', ionomer membrane 134 is wetted by solution 152, which is contained in reservoir 156. In FIG. 4, electrolyte solution and reservoir 109 were placed on the same side of substrate 111 as electrode 103. Although the electrolyte solution wetted ionomer membrane 105 to enhance the sensitivity of sensor 66 in the same manner as solution 152 enhances the sensitivity of sensor 66', reservoir 109 being on the same side of substrate 111 inhibits a length L of diffusion hole 120 from being reduced, which would reduce gas diffusion time and thereby improve sensor sensitivity. As shown in FIG. 4, length L could not be shortened more than height H of reservoir 109. Therefore, time required for gas to diffuse from the inlet through diffusion hole 120 to contact electrode 103 was difficult to reduce due to the length L of diffusion hole being of a minimum dimension not less than the height H of reservoir 109.

Sensor 66' of FIG. 5 overcomes this disadvantage by wetting ionomer membrane 134, via hole 136 in substrate 132, with solution 152 located on a side of substrate 132 opposite from electrode 138. Because of the position of reservoir 156, length L' can be shortened, thereby reducing gas diffusion time and improving the sensitivity of sensor 66'. The more length L' is reduced, the faster the response time of sensor 66'. In some embodiments, length L' is less than 1.4 mm. In other embodiments, length L' is less than 1 mm. In further, embodiments, length L' is less than 0.5 mm. In still further embodiments, length L' is less than 0.1 mm. In fact, length L' or a thickness of ionomer membrane 134 may be reduced until it is flush with or below a surface of electrode 138. In some embodiments, diffusion hole 144 is eliminated because length L' is flush with or below a surface of electrode 138. All that is required is for ionomer membrane 134, of any length L', to be in contact with electrode 138 so that gas entering through inlet 142 provide a desired gas/ionomer membrane/electrode interface.

As a result of the reduced length L' of sensor 66', the response time of sensor 66' is less than approximately 2 seconds, more preferably less than approximately 1 second, and most preferably less than approximately 0.5 seconds. In some embodiments, the response time is less than approximately 0.1 seconds.

To further enhance sensitivity, a thickness of substrate 132 is reduced to improve wetting by solution 152. Substrate 132 is of an electrically non-conductive material for providing a surface upon which electrode 138 is placed. Optionally, substrate 132 is a thin foil having insulative, or electrically non-conductive, properties. The foil is not metallic or conductive. The foil may also be flexible as compared to ceramic or glass. The thickness of the foil, or substrate 132, is generally less than approximately 4 mils and preferably less than approximately 1 mil. The thinner substrate 132, the faster ionomer membrane 134 is wetted and this positively affects sensor response time. Therefore, as the thickness of substrate 132 approaches 0 mils, the response time is further reduced.

Optionally, in some embodiments, sensor 66' may include wicking material 154 to facilitate or enhance wetting of ionomer membrane 134 by solution 152. Wicking material 154 is typically of a material that absorbs liquid, such as a sponge. Hence, as shown in FIG. 5, wicking material 154 will draw solution 152 upwardly from reservoir 156 toward ionomer membrane 134.

As shown, reservoir 156 and substrate 132 are separable from one another where wicking material 154 is placed between reservoir 156 and substrate 132. In other embodiments, wicking material is placed within reservoir 156 and reservoir comes in contact with substrate 132. In further embodiments, substrate 132 and reservoir 156 are made not separable from one another but are formed as one unit. Wicking material 154 may optionally be used with any of these embodiments of reservoir 156 and substrate 132.

As shown in FIG. 5, substrate 132 further includes at least one hole 136 extending from a first surface 162 of substrate 132 to a second surface 164 of substrate 132, thereby forming a thru-hole, for permitting solution 152 to pass, or diffuse, through at least one hole 136 to contact ionomer membrane 134. In the embodiments where substrate 132 is a foil, or a thin non-conductive material, wicking material 154 would be positioned in a closer relationship to ionomer membrane 134 than where substrate 132 is of a thick material. Where substrate 132 is a foil, solution 152 absorbed by wicking material 154 would more easily wet ionomer membrane 134. Optionally, wicking material 154 would be in contact, through at least one hole 136, with ionomer membrane 134. In some embodiments, wicking material 154 in addition to or instead of being between substrate 132 and solution 152, is placed within at least one hole 136.

To further facilitate wetting of ionomer membrane 134 by solution 152, or optional wicking material 154, a plurality of holes 136 are placed in substrate 132. It is understood that hole 136 is of any diameter, length, shape, or dimension. Also, the more holes 136 in substrate 132, in any location, the better ionomer membrane 134 is wetted. Hence, the hole 136 or plurality of holes 136 may act as a form of wetting control to ionomer membrane 134, as too much wetting or too little wetting negatively affects sensitivity. Moreover, hole 136 may be, in addition or instead of being round, a square shaped or polygonal shaped hole. Hole 136 may further be a slit or aperture of any kind. All that is required of hole 136 is that it provides a passage from first surface 162 to second surface 164 so that solution 152 diffuses through hole 136 to contact ionomer membrane 134.

Figure 6:
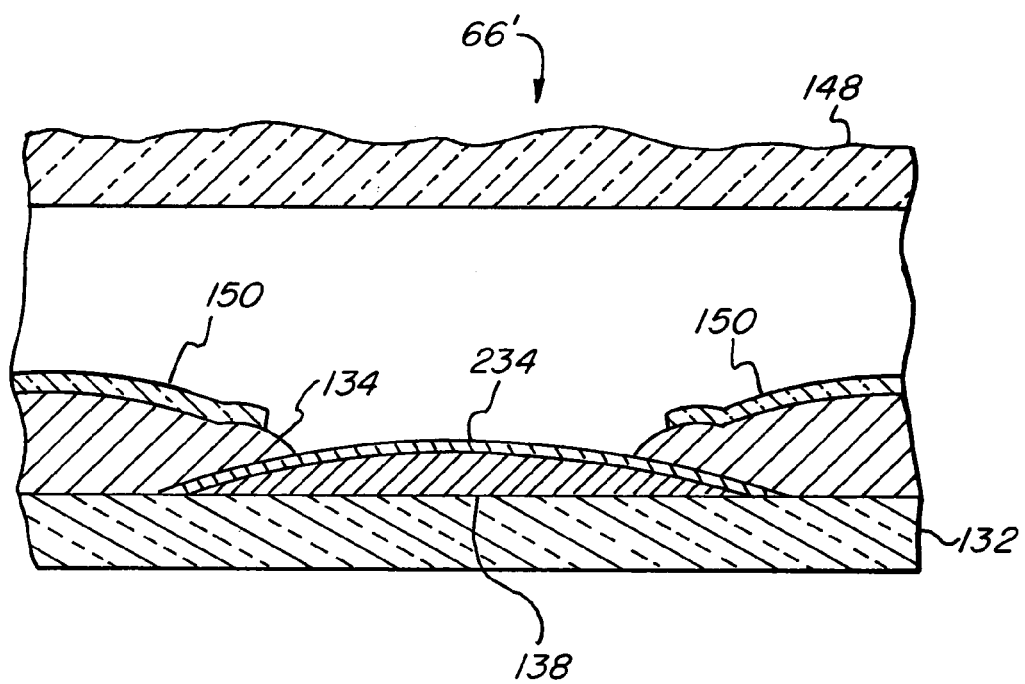
FIG. 6 depicts an exploded view of the electrode shown in FIGS. 4 and 5.

FIG. 6 depicts an exploded view of the electrode shown in FIGS. 4 and 5. As shown, to enhance sensitivity of sensor 66 or 66' in some embodiments, a thin film 234 of electrolytic material, which may be the same material as the ionomer membranes of FIGS. 4 and 5, may optionally be placed on electrode 103 or 138 to increase the area of contact between the ionomer membrane 105 or 134, electrode 103 or 138, and gas to include the surface of electrode 103 or 138. Gas diffuses throughout film 234, which is in contact with the surface of electrode 103 or 138. As a result of the increased contact area, the sensing area is increased and response time is minimized. Gas diffuses faster through film 234 when film 234 has a minimal thickness. Hence, the thinner film 234 is, the faster the response time is for sensor 66 or 66'.

Without film 234, the interface in the approximate area of electrode 103 or 138 would be substantially smaller, limited to an area where ionomer membrane 105 or 134 comes in contact with electrode 103 or 138. This contact area would generally be a linear contact point defining an approximate circumference of electrode 103 or 138.

In some embodiments, film 234 has a thickness less than 2 micrometers. Ideally, film 234 should be as thin as possible to maximize sensor response time and sensitivity. Hence, sensor 66 or 66' may further comprise film 234 having a thickness of less than 1 micrometer. A film having such reduced thickness permits faster gas diffusion and, thus, faster response times. Film 234 is an electrolytic medium, which includes all the limitations of ionomer membrane 105 or 134 and may be, but need not be, the same material as ionomer membrane 105 or 134.

Film 234 is in a solid state or dry electrolyte for it has more structural integrity than liquid state electrolyte, thereby permitting a consistently uniform thickness over electrode 103 or 138. This enhances sensor repeatability and facilitates functionality for liquid state electrolyte would be difficult to maintain in a fixed position on the surface of electrode 103 or 138.

Optionally, the response time of sensor 66 or 66' may further be improved by reducing the size of the inlet and outlet of each sensor 66 or 66'. In this effort, the gas is more concentrated while inside the sensor due to there being less internal volume for the gas to disperse. Less dispersion and a more concentrated gas generally results in a more easily detected gas and, therefore, reduced response time of sensor 66 or 66'. Hence, the volume in which gas may disperse is reduced. Such dispersion is generally referred to as axial dispersion because the dispersion is approximately along the axis containing a center point of sensor 66 or 66'. In some embodiments, the inlet and outlet have a diameter of approximately 1 mm. The inlet and outlet need not be round but may be of any shape so long as gas may be injected into and extracted from sensor 66 or 66'. Such shapes include three-sided, four-sided, or polygonal geometries.

Optionally, as shown in FIGS. 5 and 6, sensor 66' of FIG. 5 may also include cover 150 on ionomer membrane 134 for minimizing the vaporization or evaporation of electrolyte solution 152 as solution 152 is absorbed and passed upwardly through ionomer membrane 134. Cover 150 is in contact with the surface of ionomer membrane 134 opposite from substrate 132. Cover 150 does not block any portion of either diffusion hole 144 or electrode 138 because doing so would hinder gas detection and negatively affect sensor sensitivity. Cover 150 is not needed for sensor 66' to operate properly and may be eliminated entirely from sensor 66'. For embodiments where sensor 66' includes cover 150, it is understood that the length L' of the diffusion path is the height of both ionomer membrane 134 and cover 150. For embodiments where sensor 66' does not include cover 150, length L' is the height of membrane 134.

Sensor 66, 67 is preferably used for detecting exiting a gas chromatograph column. However, sensors 66, 67 may also be attached to a liquid chromatograph column provided a vaporizer is placed between column 52 and sensors 66, 67.

What is claimed is:

1. A chromatography system, comprising:
    a chromatographic column for separating gases in a mixture from one another; and
    an electrochemical gas sensor coupled to said chromatographic column for detecting a gas;
    said electrochemical gas sensor further including:
    a substrate having a surface for depositing electrodes thereon;
    an ionomer membrane in contact with said surface and having a first outermost surface and a second outermost surface;
    an electrode in contact with said surface of said substrate; and
    an opening extending from said first outermost surface to said second outermost surface in a location proximate to said electrode for permitting a gas to diffuse through said opening to simultaneously contact said electrode and said ionomer membrane within said opening.

2. The chromatography system of claim 1, further comprising a reactor placed between and coupled to both said chromatographic column and said electrochemical gas sensor for oxidizing the gas.

3. The chromatography system of claim 1, wherein said opening extends from said first outermost surface to said second outermost surface of said ionomer membrane for defining walls to guide the gas to said electrode.

4. The chromatography system of claim 1, further comprising a housing for containing said substrate, said ionomer membrane, and said electrode.

5. The chromatography system of claim 4, said housing includes a gas diffusion passage in a location proximate to said electrode and having fluid connection with said opening.

6. The chromatography system of claim 5, wherein said gas diffusion passage is angled in alignment with said opening.

7. The chromatography system of claim 5, wherein said gas diffusion passage is misaligned with said opening.

8. The chromatography system according to claim 1, wherein said substrate further includes at least one hole extending from a first surface to a second surface for permitting moisture to diffuse through said at least one hole to contact said ionomer membrane.

9. The electrochemical gas sensor according to claim 8, further comprising a reservoir for containing moisture to moisten said ionomer membrane.

10. The electrochemical gas sensor according to claim 9, wherein said reservoir is located adjacent to said substrate.

11. The electrochemical gas sensor according to claim 9, wherein said reservoir is located on a side of said substrate opposite said ionomer membrane.

12. The electrochemical gas sensor according to claim 8, said at least one hole further comprising moisture, said moisture being diffused from said reservoir to said ionomer membrane.

13. The electrochemical gas sensor according to claim 9, further comprising a wicking material in contact with said second surface for drawing moisture from said reservoir toward said substrate.

14. The electrochemical gas sensor according to claim 13, wherein said wicking material is located in said at least one hole of said substrate.

15. The electrochemical gas sensor according to claim 13, wherein said reservoir is spaced apart from said second surface and said wicking material is between said second surface and said reservoir.

16. The electrochemical gas sensor according to claim 1, wherein said substrate is a foil.

* * * * *